United States Patent
Mendelovici et al.

(10) Patent No.: US 6,936,720 B2
(45) Date of Patent: Aug. 30, 2005

(54) METHOD FOR PREPARING BENZISOXAZOLE METHANE SULFONYL CHLORIDE AND ITS AMIDATION TO FORM ZONISAMIDE

(75) Inventors: Marioara Mendelovici, Rechovot (IL); Neomi Gershon, Kfar-Saba (IL); Tamar Nidam, Yehud (IL); Gideon Pilarski, Holon (IL); Greta Sterinbaum, Rishon-Lezion (IL)

(73) Assignee: Teva Pharmaceutical Industries Ltd., Petah Tiqva (IL)

( * ) Notice: Subject to any disclaimer, the term of this patent is extended or adjusted under 35 U.S.C. 154(b) by 79 days.

(21) Appl. No.: 10/373,554

(22) Filed: Feb. 24, 2003

(65) Prior Publication Data

US 2004/0014983 A1 Jan. 22, 2004

Related U.S. Application Data

(60) Provisional application No. 60/358,916, filed on Feb. 22, 2002.

(51) Int. Cl.[7] ............................................. C07D 261/20
(52) U.S. Cl. ....................................................... 548/241
(58) Field of Search .......................................... 548/241

(56) References Cited

U.S. PATENT DOCUMENTS

| | | | |
|---|---|---|---|
| 4,172,896 A | 10/1979 | Uno et al. | |
| 6,677,458 B2 * | 1/2004 | Mendelovici et al. | ....... 548/241 |

FOREIGN PATENT DOCUMENTS

JP    53-77057    7/1978

* cited by examiner

*Primary Examiner*—Fiona T. Powers
(74) *Attorney, Agent, or Firm*—Kenyon & Kenyon

(57) ABSTRACT

The present invention relates to a process of preparing benzisoxazole methane sulfonic acid-chloride (BOS—Cl) as an zonisamide intermediate via chlorination of benzisoxazole methane sulfonate. The present invention also discloses a process of preparing zonisamide via amidation of BOS—Cl. More particularly, the present invention provides a process of preparing zonisamide, comprising the steps of: a) chlorinating BOS, salts or esters thereof, with $SOCl_2$ in an organic solvent and/or in the presence of a catalyst to form BOS—Cl; and b) amidating BOS—Cl in the presence of ammonia selected from the group consisting of aqueous ammonia in a biphasic system, masked ammonia and dry ammonia to form zonisamide.

85 Claims, No Drawings

METHOD FOR PREPARING BENZISOXAZOLE METHANE SULFONYL CHLORIDE AND ITS AMIDATION TO FORM ZONISAMIDE

CROSS-REFERENCE TO RELATED APPLICATION

This application claims the benefit under 35 U.S.C. §1.119(e) of Provisional Application Ser. No. 60/358,916 filed Feb. 22, 2002, the disclosure of which is incorporated by reference in its entirety herein.

FIELD OF THE INVENTION

The invention relates to the preparation of benzisoxazole methane sulfonyl chloride (BOS—Cl). The present invention also relates to a method for preparing 1,2-benzisoxazole-3-methane sulfonamide (zonisamide) via amidation of BOS—Cl.

BACKGROUND OF THE INVENTION

Zonisamide is currently available as an anti-epileptic agent which possesses anti-convulsant and anti-neurotoxic effects. Zonisamide is also known as 1,2-benzisoxazole-3-methane sulfonamide or 3-(sulfamoylmethyl)-1,2-benzisoxazole. It has the following chemical formula:

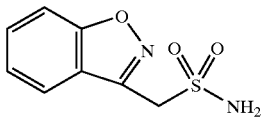

Japanese Patent 53-77057 and U.S. Pat. No. 4,172,896 describe the preparation of BOS—Cl, an intermediate in zonisamide synthesis. According to these patents, the synthesis of BOS—Cl is performed by refluxing sodium 1,2-benzisoxazole-3-methanesulfonate in $POCl_3$.

In general, acyl-halides and sulfonyl-halides are prepared by the reaction of the corresponding carboxylic acids or sulfonic acids with $POCl_3$, $PCl_5$ or $SOCl_2$. In the case of sulfonic acid sodium salts, thionyl-chloride is less reactive and the reaction requires a catalyst. In general, the conversion of sulfonyl-chloride to the corresponding sulfonyl-amide is performed with ammonia in aqueous solution or with ammonia gas.

The method of zonisamide preparation, as described in Japanese Patent 53-77057 and U.S. Pat. No. 4,172,896, uses ammonia gas to amidate the BOS—Cl in ethylacetate. An alternative method is to use aqueous ammonia. This amidation reaction is exemplified in the preparation of a zonisamide derivative having one fluorine atom in the aromatic ring.

The use of $POCl_3$ as a reagent for chlorination presents some problems for industry and poses significant health hazards. For example, $POCl_3$ is a nerve gas precursor and exposure to its vapor may result in chemical pneumonitis and pulmonary edema.

There is thus a continuing need to improve the preparation of BOS—Cl and the conversion of BOS—Cl to zonisamide.

SUMMARY OF THE INVENTION

The present invention provides a process for preparing BOS—Cl and a process for preparing zonisamide from BOS—Cl.

The present invention relates to the following steps in the process of zonisamide synthesis:

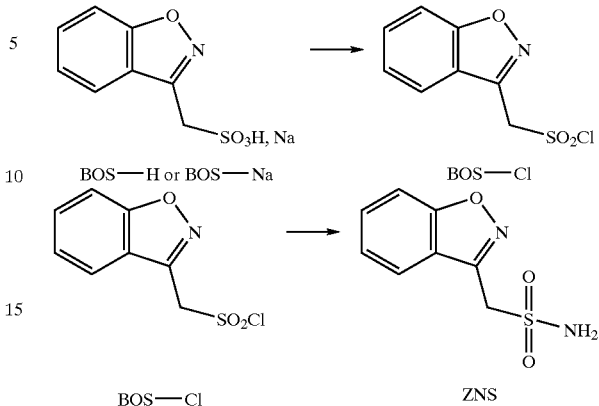

In one aspect, the present invention provides a method for preparing BOS—Cl, comprising the step of chlorinating at least one compound selected from the group consisting of BOS—H and salts and esters thereof, preferably the acid or sodium salt, with $SOCl_2$ in an organic solvent.

Optionally, the chlorination reaction is performed in the presence of a catalyst, preferably a mono-substituted or di-substituted formamide. Di-substituted formamide is more preferred. Preferably, the di-substituted formamide is substituted with at least one $C_1$ to $C_6$ alkyl group. Preferably, the di-substituted formamide is selected from the group consisting of N,N-dimethyl formamide (DMF), N,N-dipropyl formamide and N-methyl formanilide.

The present invention provides three alternative chlorinating steps.

The first alternative chlorinating step involves mixing at least one compound selected from the group consisting of BOS—H and salts and esters thereof, with a large excess of DMF and $SOCl_2$ and little or no additional solvent.

The second alternative chlorinating step involves mixing at least one compound selected from the group consisting of BOS—H and salts and esters thereof, with a large excess of $SOCl_2$ which can also function as a solvent. In this chlorinating step, a catalytic amount of DMF is used.

The third alternative chlorinating step involves mixing at least one compound selected from the group consisting of BOS—H and salts and esters thereof, with an inert organic solvent and $SOCl_2$. The chlorinating step may be performed in the presence of a catalyst. The inert organic solvent can be any inert organic solvent, including, but not limited to ethyl acetate, chlorobenzene, ethers, tetrahydrofuran (THF), methyl tert-butyl ether (MTBE), chloroform, methylene chloride, dichloroethane, dichloromethane, toluene and mixtures thereof. Preferably, the inert organic solvent is toluene. Preferably, the $SOCl_2$ is in an amount of about 2 to about 6 eq. relative to BOS—Na. More preferably, $SOCl_2$ is in an amount of about 3 to about 4 eq. relative to BOS—Na. Preferably, the catalyst is a formamide. More preferably, the formamide is a di-substituted formamide, which is most preferably DMF. Preferably, DMF is present in a catalytic amount of about 3 to about 50% mole relative to BOS—Na. More preferably, DMF is about 5 to about 30% mole relative to BOS—Na. Most preferably, DMF is about 10% mole relative to BOS—Na.

In another aspect, the present invention provides an amidating process for BOS—Cl to form zonisamide. This amidating process is applicable to BOS—Cl regardless of its sources.

In one embodiment, the present invention provides an amidating reaction for BOS—Cl in the presence of aqueous ammonia in a biphasic system. Preferably, the aqueous ammonia is about 20% wt. The biphasic system contains a first aqueous solvent phase and a second water-immiscible solvent phase. Preferably, the biphasic system comprises toluene and aqueous ammonia. Preferably, the amidating step is performed at a temperature of about 20° C.

In another embodiment, the present invention provides an amidation reaction for BOS—Cl using "masked ammonia" as an amidating agent. Preferred "masked ammonia" is an ammonium salt including ammonium carbonate, ammonium acetate, and ammonium formate. More preferably, the "masked ammonia" is ammonium carbonate. Preferably, the ammonium carbonate in present in the amount of about 3 eq. to about 10 eq. relative to BOS—Cl. Most preferably, the ammonium carbonate is present in the amount of about 5 eq. to about 6 eq. relative to BOS—Cl.

Preferably, the "masked ammonia" amidation reaction is performed in the presence of a solvent selected from the group consisting of acetone, MEK, MIBK, and ethylacetate.

Preferably, the "masked ammonia" amidation reaction is performed at a temperature of greater than about 50° C. Preferably, the amidation reaction is performed at the reflux temperature of the reaction solvent.

In another preferred embodiment, the present invention provides an amidation reaction for BOS—Cl performed under anhydrous conditions. Preferably, the anhydrous ammonia gas contains less than about 200 ppm water, more preferably, less than about 20 ppm water.

Preferably, water is minimized during both the chlorination and amidation reactions, and in the reactor itself, i.e, anhydrous conditions. Water can be removed from solvents with suitable drying agents. For example, the toluene solvent can be dried with metallic sodium or by prior azeotropic distillation techniques. Dry anhydrous ammonia gas can be prepared with $CaCl_2$, silica gel, metallic sodium, alumina, $MgSO_4$, $Na_2SO_4$, BaO or the like.

In another aspect, the present invention provides the step of crystallizing zonisamide from technical grade ethanol to reduce impurities especially ammonium salts of the hydrolysis side products.

Reducing water present during the reaction, e.g., anhydrous conditions, provides a process of preparing zonisamide which is essentially free of BOS—$NH_4$, preferably, less than about 0.1% wt BOS—$NH_4$ after crystallization. Crystallizing the zonisamide from at least 95% ethanol can further reduce the BOS—$NH_4$ to less than about 0.02% wt.

The present invention further includes the novel products of the processes disclosed here.

DETAILED DESCRIPTION OF THE INVENTION

Definitions:

As used herein, the terms "BOS" refers to benzisoxazole methane sulfonate; "BOS—Na" refers to sodium salt of BOS; "BOS—Cl" refers to benzisoxazole methane sulfonyl chloride; "$SOCl_2$" refers to thionyl chloride; "$POCl_3$" refers to phosphorus oxychloride; "ZNS" refers to zonisamide which is 1,2-benzisoxazole-3-methane sulfonamide or 3-(sulfamoylmethyl)-1,2-benzisoxazole; "MEK" refers to methyl-ethyl-ketone, "MIBK" refers to methyl-iso-butyl-ketone; "DMF" refers to dimethyl formamide; "THF" refers to tetrahydrofuran; "MTBE" refers to methyl tert-butyl ether; "eq." refers to equivalents; "ppm" refers to parts per million; "ethanol of technical grade" refers to ethanol that contains at least about 95% ethanol; and "zonisamide substantially free of BOS—$NH_4$" refers to zonisamide that contains less than about 0.1% BOS—$NH_4$.

Unless otherwise specified, % refers to % wt (i.e., % wt/wt). % mole refers to % (mole/mole).

Chlorination Reaction Steps

The first alternative chlorination step involves reacting at least one compound selected from the group consisting of BOS—H, its salts and esters, in the presence of a large excess of DMF and $SOCl_2$, with little, preferably, no other solvent. Preferably, the eq. ratio of DMF and $SOCl_2$ is in the range between about 0.5:1 to about 1:1, more preferably, about 1:1.5.

The second alternative chlorination step involves involves reacting at least one compound selected from the group consisting of BOS—H, its salts and esters, in the presence of $SOCl_2$ in large excess amount and a relatively small but catalytic amount of DMF. Here the $SOCl_2$ functions as both a chlorinating agent and a solvent.

The third alternative chlorination step involves reacting at least one compound selected from the group consisting of BOS—H, its salts and esters, and $SOCl_2$ in an inert organic solvent. The inert organic solvent can be any inert organic solvent, including, but not limited to ethyl acetate, chlorobenzene, ethers, THF, MTBE, chloroform, methylene chloride, dichloroethane, dichloromethane, toluene and mixtures thereof. Preferably, the inert organic solvent is toluene. For this alternative a catalyst is preferred but not necessary. The preferred catalyst is a di-substituted formamide. Most preferably, the catalyst is DMF. The prefered amount of DMF is about 3–50% mole relative to BOS—Na; more preferably about 5–30% mole relative to BOS—NA; and, most preferably, about 10% mole relative to BOS—Na. $SOCl_2$ is present in an excess amount; preferably, about 2–6 eq. relative to BOS—Na. The preferred amount of $SOCl_2$ is about 3–4 eq. relative to BOS—Na.

While the presence of catalyst is optional, in the presence of a catalyst $SOCl_2$ can smoothly convert BOS—Na to BOS—Cl. The preferred catalyst is formamide. Preferably, the formamide is a lower alkyl substituted formamide. Preferably, the lower alkyl formamide is a $C_1$ to $C_6$ alkyl formamide. Preferably, the substituted formamide is a mono-substituted formamide or di-substituted formamide. An example of a mono-substituted formamide is N-methyl formamide. Di-substituted formamide is a more preferred catalyst. Most preferably, the di-substituted formamide contains at least one $C_1$ to $C_6$ alkyl group. Examples of di-substituted formamides include N,N-dimethyl-formamide, N,N-dipropyl-formamide and N-methyl formanilide.

Under these conditions, the chlorination reaction proceeds with mild conditions. Preferably, the mild conditions include a reaction temperature of 50–60° C.; a solvent comprising an inert organic solvent; $SOCl_2$ and DMF catalyst in a preferred amount of about 10% mole relative to the BOS—Cl. Preferably, the $SOCl_2$ is added over a period of about 2 to about 6 hours. More preferably, $SOCl_2$ is added over a period of about 3 to about 4 hours. The inert organic solvent can be any inert organic solvent or mixture of inert organic solvents, as described above. Under these conditions, conversion to BOS—Cl is almost quantitative and the obtained zonisamide product can achieve a purity of about 95 to about 99% wt. by HPLC.

Amidation Reaction Steps

The presently disclosed amidating steps convert BOS—Cl to zonismide regardless of how the BOS—Cl is prepared. Three alternative amidation reactions are described below.

(a) Aqueous Ammonia in Biphasic System

The amidation of BOS—Cl to zonisamide may be carried out in a biphasic system. A biphasic system contains a first aqueous solvent phase and a second water-immiscible solvent phase. An example of a biphasic system includes toluene-aqueous ammonia. The BOS—Cl is dissolved in the water-immiscible solvent phase limiting its hydrolysis.

(b) Amidation with Masked Ammonia

The amidation of BOS—Cl to zonisamide using "masked ammonia" as the amidating agent. This amidation reaction is performed in an organic solvent. Preferred organic solvents include methyl-ethyl-ketone (MEK), acetone and methyl-iso-butyl-ketone (MIBK).

Preferably, the amidating reaction is performed at a temperature of between about 50° C. and about reflux temperature.

When ammonium carbonate, a preferred amidation agent, is used, the reaction side-product is carbon dioxide, which is released from the reaction mixture. The preferred amount of ammonium carbonate is about 5 equivalents calculated as free ammonia. Commercial ammonium carbonate is a mixture of ammonium carbamate and ammonium bicarbonate. The reaction temperature can be in the range of about −10° C. to about 100° C., and is preferably about 50° C.

Ammonia Gas in Anhydrous Conditions

The amidation reaction of BOS—Cl to zonisamide may be carried out using anhydrous ammonia gas as an amidating agent. The reaction temperature can be in the range of about 0 to about 25° C., preferably about 10 to about 15° C.

An advantage of using anhydrous ammonia gas as an amidating agent is that it limits the hydrolysis of BOS—Cl to BOS—$NH_4$, because the water content of ammonia is reduced. As a result, the zonisamide product obtained using anhydrous ammonia gas is substantially free of BOS—$NH_4$, preferably containing less than about 0.1% BOS—$NH_4$ after crystallization.

The hydrolysis side-reaction can be further limited by carrying out the reaction under "anhydrous conditions", i.e., minimizing water present during the reaction.

The reaction solvent, e.g., toluene, can be dried using any suitable drying agent, e.g., metallic sodium. Similarly, ammonia gas can be dried by passing it through any suitable drying agent such as $CaCl_2$, silica gel, metallic sodium, alumina, $MgSO_4$, $Na_2SO_4$, BaO or the like.

In addition, the amidation reaction can be performed in a reactor equipped with drying tubes to prevent contact of the amidating agent or solvent with the humidity present in the air. Such anhydrous conditions for amidation can improve the zonisamide yield. Preferably, the yield is about 85%. Preferably, zonisamide contains less than about 5% wt. BOS—$NH_4$; more preferably, less than about 3% wt. BOS—$NH_4$; and, most preferably, less than about 2.4% wt. BOS—$NH_4$. Comparatively, when ordinary ammonia is used, the level of side-product due to the hydrolysis reaction of BOS—Cl may reach levels as high as about 10 to about 15% wt. BOS—$NH_4$.

Crystallization of Zonisamide

The present invention further provides for crystallizing zonisamide from a solvent such as technical grade ethanol, i.e., at least about 95% ethanol, which further reduces the hydrolysis impurity to less than about 0.02% wt. BOS—$NH_4$. Preferred solvents include, but are not limited to, ethanol, absolute ethanol, methanol, isopropyl alcohol and mixtures thereof.

The present invention is described in detail below with reference to examples. The present invention is by no means restricted to these specific examples. The experiments are summarized as follows.

EXAMPLES

Example 1

Preparation of BOS—Cl in Toluene Using DMF Catalyst

A 250 mL three-necked flask was charged with toluene (100 mL), DMF (0.6 gram, 0.1 eq. relative to BOS—Na), and BOS—Na (20 grams; ~0.1 mole). The mixture was stirred at room temperature and $SOCl_2$ (32.5 grams, 3 eq. relative to BOS—Na) was added drop-wise. After the addition of $SOCl_2$, the reaction mixture was heated with stirring at about 50° C. for about 5 to about 6 hours.

After the reaction was completed, excess $SOCl_2$ was removed by flowing nitrogen gas through the reaction mixture. Fresh toluene was added and the inorganic salts were filtered out. The product BOS—Cl was obtained as a solution in toluene. Alternatively, the toluene solvent may be removed and replaced with a different appropriate solvent.

Example 2

Preparation of BOS—Cl Using Alternative Solvents/Catalysts

In the following table, additional data of the experimental procedures are shown:

| Exp. no. | Chlorination reagents, eq. | Solvent, vol. | Temp. | Purity profile (HPLC), % area Reaction mixture |
|---|---|---|---|---|
| 1† | $SOCl_2$/DMF, 1:1 | $SOCl_2$/DMF, 4 vol. | ~5° C. | 78% |
| 2† | $SOCl_2$/DMF, 1.5:1 | $SOCl_2$/DMF, 3 vol. | 5–10° C. | 83% |
| 3†† | 3 eq. $SOCl_2$/DMF | DMF, 1.5 vol. | 5–10° C. | 76% |

†In experiment nos. 1–2, solvent refers to a mixture of $SOCl_2$ and DMF. In these cases, the solvents are also the reagents.
††In experiment no. 3, DMF is the reaction solvent and $SOCl_2$ is used in a slight excess. 3 eq. $SOCl_2$ is 3 equivalents of $SOCl_2$ compared to BOS—Na.

Example 3

Preparation of Zonisamide with Aqueous Ammonia

A three-necked flask was charged with BOS—Cl (1 gram) and aqueous ammonia 20% (5 eq. relative to BOS—Cl). The reaction mixture was stirred at room temperature for about 20 hours. The product (1.2 gram) was isolated by filtration. The purity of the zonisamide product was determined to be about 95% on a HPLC.

Example 4

Preparation of Zonisamide in Toluene/Aqueous Ammonia

BOS—Cl (3 grams) was dissolved in toluene (30 mL) and ammonia 20% (5.5 grams) was added to the solution. The reaction mixture was stirred at room temperature. After 2 hours, the zonisamide product (solid) was filtered out. The HPLC of the product showed a content of about 53% zonisamide.

Example 5

Preparation of Zonisamide with Ammonium Carbonate

A three-necked flask was charged with BOS—Cl (10 grams), ammonium carbonate (20 grams) and MEK (100 mL). The reaction mixture was stirred at reflux for about 1 hour.

After cooling, the product was filtered out and washed with MEK. After drying, the zonisamide product weighed 7.13 grams (yield about 77.8%) and the purity on HPLC was 87%.

Other reaction solvents including acetone, MIBK, ethyl-acetate, butyl-acetate were used instead of MEK and were found to yield similar zonisamide products.

The crude zonisamide product was then crystallized from ethanol (~95%) to yield pure zonisamide.

Example 6

Preparation of Zonisamide with Anhydrous Ammonia a) Preparation of BOS—Cl in Toluene Using DMF as Catalyst A 1 L three-necked flask was charged with toluene (500 mL), DMF (15 grams, 0.1 eq. relative to BOS—Na), and BOS—Na (500 grams). The mixture was heated to 50–60° C. with stirring, and $SOCl_2$ (942.5 grams, 4 eq. relative to Bos—Na) added drop-wise over a period of about 3 hours. After the addition of $SOCl_2$, the reaction mixture was stirred and the temperature maintained at about 50° C. for about 4 to about 5 hours.

After the reaction was completed, excess $SOCl_2$ was removed by flowing nitrogen gas through the reaction mixture. Fresh toluene was added and the inorganic salts were filtered out. The product BOS—Cl was obtained as a solution in toluene.

b) Preparation of Zonisamide With Anhydrous Ammonia (<20 ppm Water)

A 2 L reactor was charged with the solution of BOS—Cl in toluene prepared in example 6(a). The mixture was cooled to 10–15° C. and anhydrous ammonia gas was bubbled through the mixture. The temperature of the mixture was maintained at 10–15° C. The amidation reaction was monitored by HPLC.

After the reaction was completed the inorganic salts were filtered out. The solid was reslurried (triturated) in water at room temperature, filtered and washed with 95% ethanol to provide crude product zonisamide (wet crude: 166 grams; yield: 91.25%; content of BOS—$NH_4$: 2.5% (wt/wt)).

c) Preparation of Crystallized Zonisamide

Zonisamide wet crude from the previous step (example 6(b)) was dissolved in 95% ethanol at the reflux temperature. The hot solution was then treated with 5% (w/w) active carbon for color improvement and gradually cooled to ~5° C. over a period of about 5 hours. The crystallized material was filtered out, washed with ethanol and dried at about 60° C. (yield: 90.8%; content of BOS—$NH_4$: 0.02% (w/w)).

Example 7

Preparation of Zonisamide Under Anhydrous Conditions a) Anhydrous Condition

Anhydrous conditions were achieved by drying the solvent used in the chorinating reaction as well as solvent and ammonia gas used in the amidating reaction. The chlorinating reaction solvent and amidating solvent, e.g., toluene, were dried with metallic sodium. The ammonia gas was dried by passing the gas through a $CaCl_2$ drying agent. Both the chlorinating and amidating reactions were performed in a reactor equipped with drying tubes to prevent contact with humidity in the air.

b) Preparation of BOS—Cl in Toluene Using DMF as Catalyst

A 1 L three-necked flask was charged with dry toluene (500 mL), dry DMF (15 grams, 0.1 eq. relative to BOS—Na), and BOS—Na (500 grams). The mixture was stirred at room temperature and $SOCl_2$ (942.5 grams, 4 eq. relative to BOS—Na) was added drop-wise. After the addition of $SOCl_2$, the reaction mixture was heated with stirring at about 50° C. for about 5 to about 6 hours.

After the chlorination reaction was completed, excess $SOCl_2$ was removed by vacuum distillation, the temperature being maintained at below 30° C. Fresh toluene was added and the inorganic salts were filtered out. The product BOS—Cl was obtained as a solution in toluene.

c) Preparation of Zonisamide With Anhydrous Ammonia

A 2L reactor was charged with the solution of BOS—Cl in toluene prepared in example 7(b). The mixture was cooled to 10–15° C. and anhydrous ammonia gas was bubbled through the mixture. The temperature of the mixture was maintained at 10–15° C. The amidation reaction was monitored by HPLC.

After the amidation reaction was completed, the inorganic salts and zonisamide were filtered out. The solid was reslurried (triturated) in water at room temperature, filtered and washed with 95% ethanol to provide the crude product zonisamide (yield: 85%; BOS—$NH_4$: 2.4% (wt/wt)).

Similar results were obtained when ammonia gas was dried using drying agents including silica gel, metallic sodium, alumina, $MgSO_4$, $Na_2SO_4$, and BaO.

d) Preparation of Crystallized Zonisamide

Zonisamide wet crude from the previous step (example 7(c)) was dissolved in 95% ethanol (technical ethanol) at the reflux temperature. The hot solution was then treated with 5% (w/w) active carbon for color improvement and gradually cooled to ~5° C. The crystallized material was filtered out, washed with ethanol and dried at about 60° C. (yield: 90.8%; content of BOS—$NH_4$: 0.02% (w/w)).

The invention has been described in reference to its preferred embodiment. From this description, those skilled in the art may appreciate changes that could be made in the invention which do not depart from the spirt and scope of the invention.

What is claimed is:

1. A process of preparing benzisoxazole methane sulfonyl chloride, comprising the step of chlorinating at least one compound selected from the group consisting of benzisoxazole methane sulfonic acid and salts and esters thereof, with $SOCl_2$ in an organic solvent.

2. The process according to claim 1, wherein the compound is benzisoxazole methane sulfonic acid.

3. The process according to claim 1, wherein the compound is sodium benzisoxazole methane sulfonate.

4. The process according to one of claims 1–3, wherein the organic solvent is formamide.

5. The process according to claim 4, wherein the formamide is a di-substituted formamide.

6. The process according to claim 5, wherein the di-substituted formamide comprises at least one $C_1$–$C_6$ alkyl substituent.

7. The process according to claim 6, wherein the di-substituted formamide is dimethyl formamide.

8. The process according to claim 7, wherein the eq. ratio of $SOCl_2$ and dimethyl formamide is about 0.5:1.

9. The process according to claim 7, wherein the eq. ratio of $SOCl_2$ and dimethyl formamide is about 1:1.

10. The process according to claim 7, wherein the eq. ratio of $SOCl_2$ and dimethyl formamide is about 1.5:1.

11. The process according to claim 7, wherein the eq. ratio of $SOCl_2$ and dimethyl formamide is about 3:1.

12. A process of preparing benzisoxazole methane sulfonyl chloride, comprising the step of chlorinating at least one compound selected from the group consisting of benzisoxazole methane sulfonic acid and salts and esters thereof, with $SOCl_2$ in an inert organic solvent and in the presence of a catalyst.

13. The process according to claim 12, wherein the compound is benzisoxazole methane sulfonic acid.

14. The process according to claim 12, wherein the compound is sodium benzisoxazole methane sulfonate.

15. The process according to one of claims 12–14, wherein the inert organic solvent is selected from the group consisting of ethyl acetate, chlorobenzene, ethers, tetrahydrofuran, methyl t-butyl ether, chloroform, methylene chloride, dichloroethane, dichloromethane, toluene and mixtures thereof.

16. The process according to claim 15, wherein the inert organic solvent is toluene.

17. The process according to claim 12, wherein the catalyst is formamide.

18. The process according to claim 17, wherein the formamide is a lower alkyl substituted formamide, wherein the lower alkyl is $C_1$–$C_6$.

19. The process according to claim 18, wherein the lower alkyl substituted formamide is mono-substituted.

20. The process according to claim 19, wherein the lower alkyl substituted formamide is N-methyl formamide.

21. The process according to claim 18, wherein the lower alkyl substituted formamide is a di-substituted formamide.

22. The process according to claim 21, wherein the di-substituted formamide comprises at least one $C_1$–$C_6$ alkyl substituent.

23. The process according to claim 21, wherein the di-substituted formamide is selected from the group consisting of dimethyl formamide, N,N-dipropyl formamide, and N-methyl formanilide.

24. The process according to claim 23, wherein the di-substituted formamide is dimethyl formamide.

25. The process according to claim 24, wherein the compound is sodium benzisoxazole methane sulfonate and the $SOCl_2$ is about 2 to about 6 eq. relative to the sodium benzisoxazole methane sulfonate.

26. The process according to claim 24, wherein the compound is sodium benzisoxazole methane sulfonate and the $SOCl_2$ is about 3 to about 4 eq. relative to the sodium benzisoxazole methane sulfonate.

27. The process according to claim 24, wherein the dimethyl formamide is about 3 to about 50% mole relative to the sodium benzisoxazole methane sulfonate.

28. The process according to claim 24, wherein the dimethyl formamide is about 5 to about 30% mole relative to the sodium benzisoxazole methane sulfonate.

29. The process according to claim 24, wherein the dimethyl formamide is about 10% mole relative to the sodium benzisoxazole methane sulfonate.

30. The process according to claim 24, wherein the inert organic solvent is toluene and wherein the chlorinating step is performed at a temperature between room temperature and the reflux temperature of toluene.

31. The process according to claim 24, wherein the chlorinating step is performed at about 50° to about 60° C.

32. The process according to claim 24, wherein the $SOCl_2$ is added over about 2 to about 6 hours.

33. The process according to claim 24, wherein the $SOCl_2$ is added over about 3 to about 4 hours.

34. A process of preparing zonisamide, comprising the step of amidating benzisoxazole methane sulfonyl chloride in the presence of aqueous ammonia in a biphasic system, which biphasic system contains a first aqueous solvent phase and a second water-immiscible solvent phase.

35. The process according to claim 34, wherein the first aqueous solvent phase is aqueous ammonia and the second water-immiscible solvent phase is toluene.

36. The process according to claim 35, wherein the aqueous ammonia is about 20% wt.

37. The process according to claim 36, wherein the amidating step is performed at a temperature of about 20° C.

38. The process according to claim 36, wherein the amidating step is performed for about 20 hours.

39. A process of preparing zonisamide, comprising the step of amidating benzisoxazole methane sulfonyl chloride in a solvent selected from the group consisting of acetone, methyl ethyl ketone, methyl isobutyl ketone, and ethyl acetate and in the presence of masked ammonia.

40. The process according to claim 39, wherein the masked ammonia is an ammonium salt selected from the group consisting of ammonium carbonate, ammonium acetate and ammonium formate.

41. The process according to claim 39, wherein the masked ammonia is ammonium carbonate.

42. The process according to claim 41, wherein the ammonium carbonate is about 3 to about 10 eq. relative to benzisoxazole methane sulfonyl chloride.

43. The process according to claim 41, wherein the ammonium carbonate is about 5 to about 6 eq. relative to benzisoxazole methane sulfonyl chloride.

44. The process according to claim 41, wherein the amidating step is performed at a temperature of about −10 to about 100° C.

45. The process according to claim 41, wherein the amidating step is performed at a temperature of about 50° C.

46. The process according to claim 41, wherein the amidating step is performed for about 1 hour.

47. A process of preparing zonisamide, comprising the step of amidating benzisoxazole methane sulfonyl chloride in the presence of anhydrous ammonia.

48. The process of claim 47, wherein the anhydrous ammonia is a gas.

49. The process according to claim 48, wherein the anhydrous ammonia gas contains less than about 20 ppm water.

50. The process according to claim 48, wherein the anhydrous ammonia gas contains less than about 20 ppm water.

51. The process according to claim 48, wherein the amidating step is performed at a temperature of about 0 to about 25° C.

52. A process of preparing zonisamide, comprising the step of amidating benzisoxazole methane sulfonyl chloride in the presence of anhydrous ammonia, wherein the amidating step is performed at a temperature of about 10 to about 15° C.

53. Zonisamide prepared according to the process of claim 48, wherein the zonisamide contains ammonium benzisoxazole methane sulfonate at less than about 0.1% wt.

54. Zonisamide essentially free of ammonium benzisoxazole methane sulfonate, wherein the zonisamide contains ammonium benzisoxazole methane sulfonate at less than about 0.1% wt.

55. A process of preparing zonisamide, comprising the step of amidating benzisoxazole methane sulfonyl chloride in an anhydrous solvent and in the presence of anhydrous ammonia.

56. The process of claim 55, wherein the anhydrous solvent is toluene and the anhydrous ammonia is a gas.

57. The process according to claim 56, wherein the toluene is obtained by drying toluene with metallic sodium.

58. The process according to claim 56, wherein the anhydrous ammonia gas is obtained by drying ammonia gas with a drying agent selected from the group consisting of $CaCl_2$, silica gel, metallic sodium, alumina, $MgSO_4$, $Na_2SO_4$, and BaO.

59. Zonisamide prepared according to the process of claim 55, wherein the zonisamide contains ammonium benzisoxazole methane sulfonate at less than about 5% wt.

60. Zonisamide prepared according to the process of claim 55, wherein the zonisamide contains ammonium benzisoxazole methane sulfonate at less than about 3% wt.

61. Zonisamide prepared according to the process of claim 55, wherein the zonisamide contains ammonium benzisoxazole methane sulfonate at less than about 2.4% wt.

62. A process of preparing zonisamide, comprising the steps of:
   a) chlorinating at least one compound selected from the group consisting of benzisoxazole methane sulfonic acid and salts and esters thereof, with $SOCl_2$;
   b) amidating the benzisoxazole methane sulfonyl chloride from step a) in the presence of an amidating agent selected from the group consisting of aqueous ammonia in a biphasic system, masked ammonia and dry ammonia gas; and
   c) isolating zonisaimde.

63. The process of claim 62, wherein step a) is performed in an inert organic solvent.

64. The process of claim 62, wherein step a) is performed in an inert organic solvent and in the presence of a catalyst.

65. The process according to claim 62, further comprising performing step b) under anhydrous conditions.

66. The process of claim 65, wherein step b) is performed in a reactor equipped with drying tubes.

67. The process according to claim 62, wherein the compound is benisoxazole methane sulfonic acid.

68. The process according to claim 62, wherein the compound is sodium benisoxazole methane sulfonate.

69. The process according to one of claims 62–68, wherein the inert organic solvent is selected from the group consisting of ethyl acetate, chlorobenzene, ethers, tetrahydrofuran, methyl t-butyl ether, chloroform, methylene chloride, dichloroethane, dichloromethane, toluene and mixtures thereof.

70. The process according to claim 69, wherein the inert organic solvent is toluene.

71. The process according to claim 62, wherein the catalyst is a di-substituted formamide.

72. The process according to claim 71, wherein the di-substituted formamide comprises at least one $C_1$–$C_6$ alkyl substituent.

73. The process according to claim 72, wherein the di-substituted formamide is selected from the group consisting of N,N-dimethyl formamide, N,N-dipropyl formamide, dimethyl formamide and N-methylformanilide.

74. The process according to claim 72, wherein the di-substituted formamide is dimethyl formamide.

75. The process according to claim 74, wherein the amidating agent is aqueous ammonia in a biphasic system, wherein the biphasic system contains a first aqueous solvent phase and a second water-immiscible solvent phase.

76. The process according to claim 75, wherein the first aqueous solvent phase is aqueous ammonia and the second water-immiscible solvent phase is toluene.

77. The process according to claim 74, wherein the amidating agent is masked ammonia.

78. The process according to claim 77, wherein the masked ammonia is an ammonium salt selected from the group consisting of ammonium carbonate, ammonium acetate and ammonium formate.

79. The process according to claim 74, wherein the amidating agent is an anhydrous ammonia gas.

80. The process according to claim 74, wherein the organic solvent is anhydrous toluene and the amidating agent is an anhydrous ammonia gas.

81. The process of claim 64, further comprising a step of crystallizing zonisamide.

82. The process according to claim 81, wherein the crystallizing step is performed in ethanol, absolute ethanol, methanol, isopropyl alcohol or mixtures thereof.

83. The process according to claim 82, wherein the crystallizing step is performed in ethanol, which ethanol is at least about 95%.

84. Zonisamide prepared according to the method of claim 79, wherein the zonisamide contains ammonium benzisoxazole methane sulfonate at less than about 0.1%.

85. Zonisamide prepared according to the method of claim 79, wherein the zonisamide contains ammonium benzisoxazole methane sulfonate at less than about 0.02%.

* * * * *